United States Patent [19]

Place et al.

[11] Patent Number: 5,512,299
[45] Date of Patent: Apr. 30, 1996

[54] METHOD OF TREATING ORAL INFLAMMATORY DISEASE

[75] Inventors: Virgil A. Place, Kawaihae, Hi.;
Myriam T. Encarnacion, Hayward, Calif.; Patrick S. L. Wong, Palo Alto, Calif.; Juan M. E. Harrison, Mountain View, Calif.

[73] Assignee: Alza Corporation, Palo Alto, Calif.

[21] Appl. No.: 92,024

[22] Filed: Jul. 14, 1993

Related U.S. Application Data

[63] Continuation of Ser. No. 860,478, Mar. 30, 1992, abandoned.

[51] Int. Cl.⁶ ....................................... A61K 9/20
[52] U.S. Cl. ...................... 424/464; 424/469; 424/492; 424/489; 424/494
[58] Field of Search .................................. 424/464, 468, 424/465, 451; 604/892.1; 106/260

[56] References Cited

U.S. PATENT DOCUMENTS

| | | | |
|---|---|---|---|
| 3,054,724 | 9/1962 | Roff et al. | 424/474 |
| 3,402,240 | 9/1968 | Cain et al. | 424/468 |
| 3,732,865 | 5/1973 | Higuchi et al. | 128/260 |
| 3,845,770 | 11/1974 | Theeuwes et al. | 128/260 |
| 3,854,480 | 12/1974 | Zaffaroni | 128/260 |
| 3,916,899 | 11/1975 | Theeuwes et al. | 128/260 |
| 4,111,202 | 9/1978 | Theeuwes | 128/260 |
| 4,238,475 | 12/1980 | Witzel et al. | 424/48 |
| 4,294,829 | 10/1981 | Suzuki et al. | 424/241 |
| 4,327,725 | 5/1982 | Cortese et al. | 128/260 |
| 4,478,822 | 10/1984 | Haslam et al. | 424/78 |
| 4,572,832 | 2/1986 | Kigasawa et al. | 424/19 |
| 4,612,008 | 9/1986 | Wong et al. | 604/892 |
| 4,627,971 | 12/1986 | Ayer | 424/15 |
| 4,639,368 | 1/1987 | Niazi et al. | 424/48 |
| 4,666,705 | 5/1987 | DeCrosta et al. | 424/482 |
| 4,713,243 | 12/1987 | Schiraldi et al. | 424/151 |
| 4,725,440 | 2/1988 | Ridgway et al. | 424/465 |
| 4,749,575 | 6/1988 | Rotman | 424/468 |
| 4,765,983 | 8/1988 | Takayanagi et al. | 424/434 |
| 4,783,337 | 11/1988 | Wong et al. | 424/468 |
| 4,786,503 | 11/1988 | Edgren et al. | 424/443 |
| 4,835,142 | 5/1989 | Suzuki et al. | 514/53 |
| 4,863,737 | 9/1989 | Stanley et al. | 424/440 |
| 4,871,548 | 10/1989 | Edgren et al. | 424/488 |
| 4,892,740 | 1/1990 | Takasima et al. | 424/474 |
| 4,904,474 | 2/1990 | Theeuwes et al. | 424/468 |
| 4,946,685 | 8/1990 | Edgren et al. | 424/472 |
| 4,983,394 | 1/1991 | Hussein et al. | 424/465 |
| 5,021,053 | 6/1991 | Barclay et al. | 604/892.1 |
| 5,053,032 | 10/1991 | Barclay et al. | 604/892.1 |
| 5,178,866 | 1/1993 | Wright et al. | 424/473 |
| 5,229,131 | 7/1993 | Amidon et al. | 424/451 |
| 5,248,310 | 9/1993 | Barclay et al. | 604/891.1 |

FOREIGN PATENT DOCUMENTS

| | | |
|---|---|---|
| 0375063 | 12/1989 | European Pat. Off. . |
| 0391342 | 4/1990 | European Pat. Off. . |

OTHER PUBLICATIONS

"Treatment of denture stomatitis by a sustained drug-delivery device: a preliminary study," J. Dent (1988) vol. 16, pp. 219–221. D. J. Lamb and C. W. I. Douglas.

"Candidosis of the Oral Cavity, Recognition and Management," Drugs vol. 36, pp. 633–642 (1988) K. D. Hay.

"Minor Aphthous Oral Ulcerations: A Double-Blind Cross-over Study of Beclomethasone Dipropionate Aerosol Spray", Scot Med J (1989) vol. 34, pp. 531–532.

"Treatment of Radiostomatitis with Salcoat", Gan No Rinsho, (1990), vol. 36, No. 1, pp. 66–90, Ishii, J. et al.

*Primary Examiner*—Thurman K. Page
*Assistant Examiner*—William E. Benston, Jr.
*Attorney, Agent, or Firm*—Richard T. Ito; Steven F. Stone; Edward L. Mandell

[57] ABSTRACT

A method of treating inflammatory disease of the mouth by locally delivering beclomethasone dipropionate and related compounds to the oral cavity of a patient over an extended period of time is disclosed. In one embodiment, beclomethasone dipropionate is delivered by an osmotic device (10), in another embodiment, it is delivered by an erosion controlled device (110) and in yet another embodiment, it is delivered by a diffusion controlled device (310).

22 Claims, 4 Drawing Sheets

Fig. 11
Release Rate of Beclomethasone Dipropionate

Fig. 12
Cumulative Beclomethasone Dipropionate Released

METHOD OF TREATING ORAL INFLAMMATORY DISEASE

This application is a continuation application of U.S. patent application Ser. No. 07/860,478, filed Mar. 30, 1992, now abandoned.

TECHNICAL FIELD

This invention pertains to a method of treating inflammatory disease of the mouth by locally delivering beclomethasone dipropionate and related compounds to the oral cavity of a patient over an extended period of time.

BACKGROUND ART

Beclomethasone dipropionate, a diester of beclomethasone, is a corticosteroid used as an antiallergic, antiasthmatic and topical anti-inflammatory. It is primarily used in nasal inhalers to relieve symptoms of nasal inflammation and irritation often associated with allergies, and in oral inhalers to treat symptoms of bronchial asthma.

Beclomethasone dipropionate has also been used to treat oral inflammatory disease. When treating inflammatory conditions of the mouth by administering beclomethasone dipropionate into the oral cavity, a number of conditions are present that make it difficult to effectively deliver a therapeutically effective amount for a prolonged period of time (e.g., for periods greater than several minutes). For example, when a patient applies a spray to the oral cavity, the therapeutic level of the drug exists for only a short time period. Additionally, when a patient is given a drug-containing lozenge or lollipop, there is a natural tendency to suck and chew on it thereby effectively reducing the time period during which the drug can be buccally administered by the lozenge. In addition, the action of saliva and swallowing by the patient effectively reduces the concentration of drug along the buccal membranes of the oral cavity and further causes much of the drug to be swallowed. This has been a particular problem in treating inflammatory diseases of the mouth which require constant local administration of beclomethasone dipropionate.

U.S. Pat. No. 4,863,737 describes the delivery of beclomethasone dipropionate by lollipop. As discussed above, this method of delivery is effective only for a short time period. Moreover, the patent is directed to treatment of disease by systemic delivery of beclomethasone dipropionate, rather than local treatment of inflammatory disease of the oral cavity. Accordingly, the patient is subject to the side-effects of systemic delivery of beclomethasone.

U.S. Pat. Nos. 4,835,142 and 4,294,829 and EP 0 391 342 describe the delivery of beclomethasone dipropionate by powdery and gel base sprays. Unfortunately, when a drug is administered by a spray, the drug is released at a therapeutic level for a very short period of time. Accordingly, this dosage form requires frequent repetitive dosing in order to effectively treat inflammatory disease.

U.S. Pat. No. 4,765,983 describes the delivery of beclomethasone dipropionate to the oral cavity of a patient by medical adhesive tape. Tape has a tendency to cause irritation to the patient and, accordingly, is not desirable from the standpoint of patient comfort. Moreover, since the device is adhered to the buccal membrane and maintains a high concentration of the drug at a single membrane site, the beclomethasone dipropionate is delivered systemically with the resulting side-effects. Additionally, it is difficult to treat numerous areas in the mouth using tape.

Thus, there has been a need in the art for a method of treating oral inflammatory diseases, such as stomatitis, erosion or sores, that is able to continuously locally deliver beclomethasone dipropionate for extended periods of time to the oral cavity.

DISCLOSURE OF THE INVENTION

Accordingly, it is an object of this invention to provide a method of treating oral inflammatory diseases by the controlled delivery of beclomethasone dipropionate to the oral cavity of an animal, and in particular a human, for an extended period of time.

It is another object of the invention to provide a method of treating oral inflammatory diseases by the controlled delivery of beclomethasone dipropionate at a pharmaceutically effective rate to the oral cavity of an animal, and in particular a human, for an extended period of time using an oral osmotic device.

It is another object of the invention to provide a method of treating oral inflammatory diseases by the controlled delivery of beclomethasone dipropionate at a pharmaceutically effective rate to the oral cavity of an animal, and in particular a human, for an extended period of time using an oral erosion controlled device.

It is another object of the invention to provide a method of treating oral inflammatory diseases by the controlled delivery of beclomethasone dipropionate at a pharmaceutically effective rate to the oral cavity of an animal, and in particular a human, for an extended period of time using an oral diffusion controlled device.

Other objects, features and advantages of the invention will be more apparent to those versed in the art from the following detailed specification taken in conjunction with the figures and the accompanying claims.

The term "beclomethasone dipropionate" is used to designate both the actual compound and the related compounds thereof. While the preferred active agent according to the present invention is beclomethasone dipropionate itself, the invention also includes analogs, homologs, agonists, antagonists and other compounds related to beclomethasone dipropionate. Numerous analogs, homologs, agonists, antagonists and other compounds related to beclomethasone dipropionate are known in the art, representatives of which are disclosed in, for example, GB Patents Nos. 912,378 and 901,093, which are incorporated by reference.

This invention concerns a method of treating oral inflammatory disease by controlled local delivery of beclomethasone dipropionate to the oral cavity of a human for an extended period of time. One method of treatment comprises local delivery of beclomethasone dipropionate using an oral osmotic device. Another method of treatment comprises local delivery of beclomethasone dipropionate using an erosion controlled device. Yet another method of treatment comprises local delivery of beclomethasone dipropionate using a so diffusion controlled device. Each device has a size and shape allowing it to be comfortably retained in the oral cavity for an extended period of time.

DETAILED DESCRIPTION OF THE INVENTION AND PREFERRED EMBODIMENTS

Figure 1:
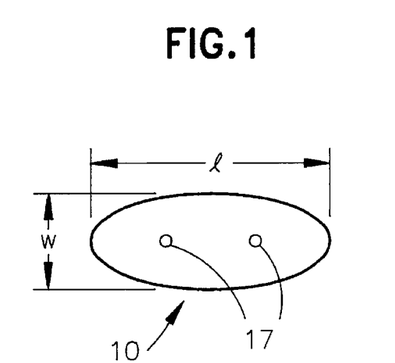
FIG. 1 is a top view of a preferred embodiment of an osmotic device for administering beclomethasone dipropionate into the oral cavity of an animal.
Figure 2:
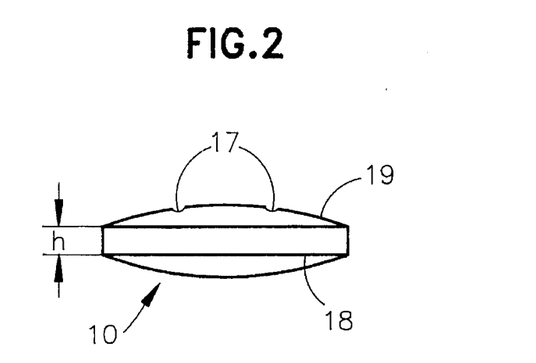
FIG. 2 is a side view of the oral osmotic device shown in FIG. 1.

Turning now to the drawings, an osmotic device suitable for a method of treating oral inflammatory disease by the controlled local delivery of beclomethasone dipropionate into the oral cavity for an extended period of time is shown in FIGS. 1 and 2, and is indicated by the numeral 10. Device 10 has a wall 12 that surrounds and forms a compartment 13, as seen in the sectional views of FIGS. 3 and 4. Wall 12 is formed of a polymeric material that is substantially permeable to the passage of saliva and substantially impermeable to the passage of beclomethasone dipropionate. The polymer forming wall 12 is non-toxic and it maintains its physical and chemical integrity during the life of device 10. Device 10 delivers beclomethasone dipropionate through one or more passageways 17 through wall 12.

Figure 3:
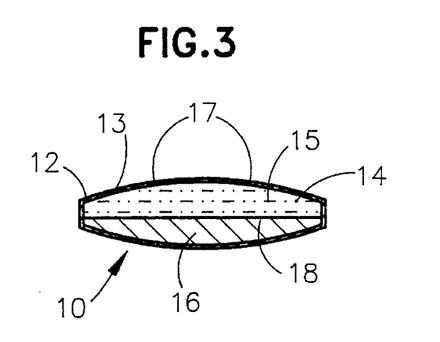
FIG. 3 is a side sectional view of the osmotic device of FIGS. 1 and 2, illustrating the internal structure of the device.
Figure 4:
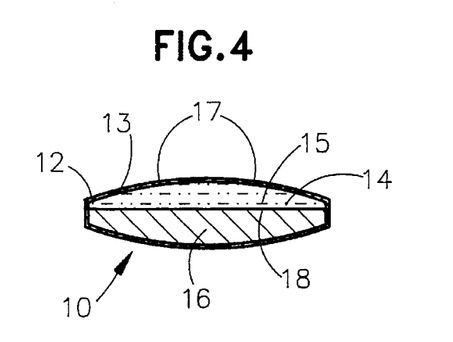
FIG. 4 is a side sectional view of the osmotic device of FIG. 3 after delivering a portion of beclomethasone dipropionate from the device.

Compartment 13 comprises a layer of beclomethasone dipropionate 14, indicated by dots, that has a limited solubility in an exterior aqueous fluid (e.g., salvia) 15, indicated by dashes. Compartment 13 further houses a layer of an expandable driving member 16 composed of a hydrophilic polymer, optionally cross-linked, which possesses osmotic properties such as the ability to imbibe external fluid and exhibit an osmotic pressure gradient across the wall 12 against the fluid. Wall 12 is substantially impermeable to the passage of the hydrophilic polymer in driving layer 16. Layer 16 absorbs fluid imbibed into the compartment and swells. The osmotic pressure of the hydrophilic polymer network is the driving force of the swelling, expanding layer 16. Layer 16 is in contact with the beclomethasone dipropionate layer 14 at the interface 18 formed by the hydrophilic polymer and beclomethasone dipropionate. Interface 18 can be achieved by maintaining a difference in the viscosity values of layers 14 and 16. For example, layer 16 can be formulated with a hydrophilic polymer having a high molecular weight and a high degree of cross-linking, such that there is negligible penetration of beclomethasone dipropionate 14 into layer 16.

Device 10 releases beclomethasone dipropionate 14 through one or more passageways 17 in wall 12 that communicates beclomethasone dipropionate 14 with the exterior of device 10. Device 10 releases beclomethasone dipropionate 14 by fluid being imbibed into compartment 13 in a tendency towards osmotic equilibrium at a rate determined by the permeability of wall 12 and the osmotic pressure gradient across wall 12. The imbibed fluid continuously forms a solution of osmagent containing beclomethasone dipropionate 14 in suspension, which solution is released by the combined operation of device 10. These operations include the suspension being osmotically delivered through passageways 17, due to the continuous formation of suspension in the compartment 13, and by the hydrophilic polymer layer 16 swelling and applying pressure against the suspension, thereby delivering it to the exterior of device 10.

Compartment 13 operates to substantially insure that delivery of beclomethasone dipropionate 14 from compartment 13 is constant over a prolonged period of time by two methods. First, hydrophilic polymer layer 16 operates to continuously concentrate beclomethasone dipropionate 14 by imbibing some fluid from beclomethasone dipropionate 14 to keep the concentration of beclomethasone dipropionate 14 from falling below saturation. Secondly, layer 16 by imbibing external fluid 15 across wall 12 continuously increases its volume, as illustrated by the expansion of layer 16 from that shown in FIG. 3 to that shown in FIG. 4, thereby exerting a force on beclomethasone dipropionate 14 and diminishing the volume of beclomethasone dipropionate 14, thus concentrating beclomethasone dipropionate 14 in compartment 13. The swelling of layer 16, along with the simultaneous, corresponding reduction of volume of beclomethasone dipropionate 14, assures the delivery of beclomethasone dipropionate 14 at a controlled rate over time.

Osmotic delivery device 10 has a mechanism for displaying the amount of beclomethasone dipropionate formulation remaining in the device for delivery into the patient. In one preferred embodiment, the display means comprises color contrast between the beclomethasone dipropionate formulation 14 and the driving layer 16, in combination with a translucent wall 12. In this embodiment, the color of the beclomethasone dipropionate formulation 14 is chosen to provide good visual contrast with the color of the driving layer 16. The color of the beclomethasone dipropionate formulation 14 can be achieved using any number of coloring techniques known in the art. For example, beclomethasone dipropionate may adequately contrast with the natural color of the driving layer 16. On the other hand, a number of pharmaceutically acceptable dyes or coloring agents may be mixed with either the beclomethasone dipropionate formulation 14 and/or the driving layer 16 in order to provide the appropriate color contrast. Suitable pharmaceutically acceptable coloring agents, both natural and synthetic, are known in the art. See *Remington'Pharmaceutical Sciences*, 14th Ed., pp 1319–1321.

In accordance with this embodiment of the invention, the patient can easily determine the amount of beclomethasone dipropionate 14 remaining in compartment 13 simply by visually inspecting device 10. For example, the beclomethasone dipropionate formulation 14 may have a white color and driving layer 16 may be dyed to achieve a red color. When the device is first placed in the mouth of the patient, the white and red layers are clearly visible through the translucent semipermeable wall 12. After a period of time in the patient's mouth, the device 10 will imbibe aqueous fluid (e.g., saliva), thereby causing suspension of the beclomethasone dipropionate 14 to be formed and also causing the hydrogel 16 layer to expand. Because the beclomethasone dipropionate layer and the s hydrophilic polymer layer have contrasting colors, the patient can easily determine the relative amount of beclomethasone dipropionate remaining in the device for delivery.

In another embodiment, a plurality of lines 19 are provided on wall 12. Each of the lines 19 is positioned to align with interface 18 after the device 10 has been retained in the mouth for a predetermined period of time, e.g., a one hour marking line, a two hour marking line, etc. In this way, the patient can easily monitor the duration of beclomethasone dipropionate delivery, even without access to a clock.

In another preferred embodiment of the present invention, the mechanism for signaling the patient comprises a contrast in taste between the beclomethasone dipropionate formulation 14 and the hydrophilic polymer driving layer 16. In this embodiment, the flavor of the beclomethasone dipropionate formulation 14 is chosen to provide a sharp contrast with the flavor of the hydrophilic polymer driving layer 16. Preferably, the beclomethasone dipropionate formulation contains a flavoring agent which is enjoyed by the patient, while the hydrophilic polymer layer contains a flavoring agent having an unpleasant taste. For example, the beclomethasone dipropionate can be flavored with peppermint oil while the hydrophilic polymer layer is flavored with a salt (e.g., NaCl). The flavor of the beclomethasone dipropionate formulation 14 can be achieved by any number of flavoring techniques known in the art. For example, a number of pharmaceutically acceptable flavoring agents may be mixed with either the beclomethasone dipropionate formulation 14 and/or the hydrophilic polymer in layer 16, in order to provide the appropriate taste contrast. Suitable pharmaceutically acceptable flavoring agents, both natural and synthetic, are known in the art. See *Remington's Pharmaceutical Sciences*, 14th Ed., pp 1321–1338.

In another embodiment of the invention, a flavoring agent is incorporated in wall 12. Preferably, wall 12 contains a flavoring agent that leaches out into the salvia as soon as the device is placed in the patient's mouth. Most preferably, wall 12 contains a flavoring agent that is enjoyed by the patient and, in particular, can be the same flavoring agent used to flavor the beclomethasone dipropionate formulation 14. Any of the pharmaceutically acceptable flavoring agents mentioned above may be incorporated into wall 12.

Osmotic delivery device 10 can be manufactured with a wall 12 formed of a material that does not adversely affect beclomethasone dipropionate layer 14, the osmagent, if any is present, and the hydrophilic polymer in layer 16. The material forming wall 12 should also not adversely affect the buccal tissues of the patient. In addition, the material forming wall 12 is permeable to the passage of an external aqueous fluid 15, such as water and biological fluids naturally present in the oral cavity (e.g., saliva), while remaining essentially impermeable to the passage of hydrophilic polymer, and optionally impermeable to the passage of agents, including beclomethasone dipropionate, osmagents, and the like. The selectively semipermeable materials forming wall 12 are insoluble in fluids naturally present in the oral cavity. Typical materials for forming wall 12 include semipermeable polymers known to the art as osmosis and reverse osmosis membranes, such as those described in U.S. Pat. No. 5,021,053, column 9, line 29 to line 59 and in U.S. Pat. No. 5,082,668, column 10, line 10 to column 14, line 34. Generally, semipermeable materials useful for forming wall 12 will have a fluid permeability of $10^{-5}$ to $10^{-1}$ (cc·mil/cm$^2$·hr·atm) expressed per atmosphere of hydrostatic or osmotic pressure difference across semipermeable wall 12. In another embodiment of the invention, the wall 12 has an overcoating containing beclomethasone dipropionate.

In accordance with one preferred embodiment of the present invention, at least a portion of the material forming wall 12 is sufficiently translucent to allow a patient to see the relative amounts of hydrophilic polymer 16 and beclomethasone dipropionate 14 remaining in compartment 13. Examples of suitable translucent materials include the cellulosic polymers. Generally, the wall 12 will contain a sufficient amount of translucent material to enable the patient to see the beclomethasone dipropionate layer 14 and the hydrophilic polymer layer 16 within compartment 13. Suitable amounts of translucent materials will depend upon the translucency of the wall material, the methods and conditions under which the wall materials are formed, as well as the amount of contrast in the colors of the beclomethasone dipropionate and hydrogel layers. Suitable amounts of translucent materials can be easily determined through routine experimentation using the examples herein.

In order to withstand the conditions of use within the oral cavity (i.e., patient sucking of the delivery device), the beclomethasone dipropionate layer 14 should contain a gelling or suspending agent which prevents the exterior wall from collapsing during use, as described in U.S. Pat. No. 5,021,053, column 11, line 55 to line 63. Generally, the beclomethasone dipropionate layer 14 typically contains from about 0.5 weight percent ("wt. %") to about 99.9 wt. % of a gelling or suspending agent, depending on the loading of beclomethasone dipropionate in layer 14. Preferably, the gelling or suspending agent is polyvinyl pyrrolidone, hydroxy propyl methyl cellulose, hydroxy propyl cellulose, mannitol or mixtures thereof.

There can also be present in compartment 13, a binder, dispersant, wetting agent and lubricant or mixtures thereof. Representative of these include binders like polyvinyl pyrrolidone and hydroxy propyl methyl cellulose, wetting agents such as fatty amines and fatty quaternary ammonium salts, preferably polyethylene glycol, and lubricants such as magnesium stearate and stearic acid. The phrase "beclomethasone dipropionate formulation" indicates beclomethasone dipropionate is present in the compartment, accompanied by a gelling or suspending agent, an osmagent, a binder, dye or the like.

An osmagent present in the device, is an osmotically effective compound soluble in the fluid that enters the device, and exhibits an osmotic pressure gradient across the semipermeable wall against the exterior fluid. Osmotically effective osmagents, useful for the present purpose, include those described in U.S. Pat. No. 5,021,053, column 12, line 31 to line 38. The osmagent is usually present in an excess amount, and it can be in any physical form, such as particle, powder, granule, and the like. The osmotic pressure in atmospheres of the osmagents suitable for the invention will be greater than zero and generally up to about 500 atm, or higher. Preferably, the osmagent is kappa carrageenan, sorbitol, KCl, NaCl or mixtures thereof.

The hydrophilic polymer layer 16 suitable for the purpose of the invention are swellable, hydrophilic polymers which interact with water and aqueous biological fluids and swell or expand to an equilibrium state. The polymers exhibit the ability to swell in water and retain a significant portion of the imbibed water within the polymer structure. The polymers swell or expand to a very high degree, usually exhibiting a 2 to 50 fold volume increase. The polymers can be noncross-linked or cross-linked. The swellable, hydrophilic polymers are in one presently preferred embodiment lightly cross-linked, such cross-links being formed by covalent, ionic bonds or hydrogen bonds. The polymers can be of plant, animal or synthetic origin. Suitable hydrophilic polymers are described in U.S. Pat. No. 5,021,053, column 12, line 57 to column 13, line 23. Preferably, the hydrophilic polymers are polysaccharides. Exemplary polysaccharides include linear or branched polysaccharides, or a polysaccharide with basic, carboxyl or other acid groups. Typical polysaccharide agents are described in U.S. Pat. No. 4,725,272, column 5, line 58 to line 66, including kappa carrageenan.

The interaction of the hydrophilic polymer-beclomethasone dipropionate interface can be ascertained by placing a film formed of a hydrophilic polymer in contact with an aqueous solution containing beclomethasone dipropionate, and sometimes an osmagent, and observing the modification of the polymer at the polymer-aqueous environment as described in U.S. Pat. No. 5,021,053, column 13, line 51 to line column 14, line 7. The device of the invention is manufactured by standard techniques as described in U.S. Pat. No. 5,021,053, column 14, line 8 to line 61.

The expression "passageway", as used herein, comprises means and methods suitable for releasing the agent from the system. The expression includes one or more aperture, orifice or bore through wall 12 formed by mechanical procedures, or by eroding an erodible element, such as a gelatin plug, in the oral cavity. In cases where the semipermeable membrane is sufficiently permeable to the passage of beclomethasone dipropionate, the pores in the membrane may be sufficient to release beclomethasone dipropionate in therapeutically effective amounts. In such cases, the expression "passageway" refers to the pores within the membrane wall, even though no bore or other orifice has been drilled therethrough. A detailed description of osmotic passageways and the maximum and minimum dimensions for a passageway are disclosed in U.S. Pat. Nos. 3,845,770 and 3,916,899, the disclosures of which are incorporated herein by reference. Preferably, one to two passageways 17 are provided in device 10 as shown in FIGS. 1–4, more preferably, one passageway is provided having a diameter of about 15 mils to about 30 mils.

Figure 5:
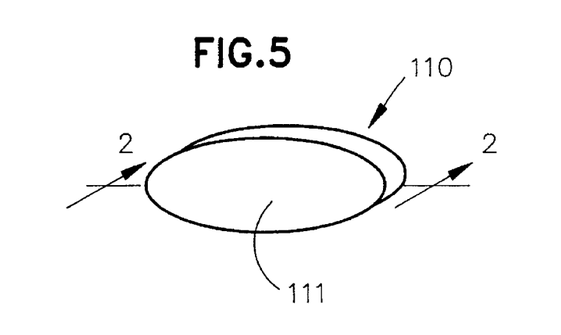
FIG. 5 is a top view of an erosion controlled device for administering beclomethasone dipropionate into the oral cavity of an animal.

An oral erosion device suitable for a method of treating oral inflammatory disease by the controlled local delivery of beclomethasone dipropionate into the oral cavity for an extended period of time is shown in FIGS. 5–8. In FIG. 5, oral erosion device 110 comprises body 111 that is non-toxic and does not adversely affect the buccal tissues of the patient.

Figure 6:
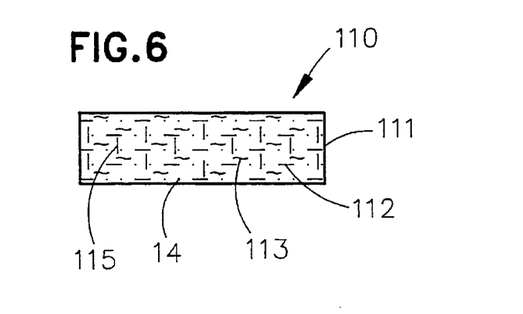
FIG. 6 is a side sectional view of the erosion controlled device of FIG. 5 illustrating the internal structure of the device.

In FIG. 6, oral erosion device 110 is seen in cross-section through 2—2 of FIG. 5. In FIG. 5, device 110 comprises body 111 comprising a cellulosic ether formulation. In one embodiment, the cellulosic ether formulation comprises a low number average molecular weight hydroxy propyl methyl cellulose ether 112, represented by dashes, and a high number average molecular weight hydroxy propyl methyl cellulose ether 113, represented by wavy lines. In another embodiment, device 110 comprises a low number average molecular weight hydroxy propyl methyl cellulose ether 112, a high number average molecular weight hydroxy propyl methyl cellulose ether 113, and a hydroxy propyl cellulose 115, represented by vertical lines.

In an embodiment of the invention, device 110 comprises from 30% to 99.9% of a cellulosic ether formulation. This cellulosic ether formulation comprises from 5% to 80% of a low number average molecular weight cellulose ether, and from 15% to 90% of a high number molecular weight hydroxy propyl methylcellulose. In another embodiment, device 110 comprises from 30% to 99.9% of a cellulosic ether composition which composition comprises from 5% to 80% of a low number average molecular weight hydroxy propyl methyl cellulose, from 10% to 90% of a high number molecular weight hydroxy propyl methyl cellulose and from 2% to 30% of a low substituted hydroxy propyl cellulose. Device 110 comprises from 0.01% to 40% of beclomethasone dipropionate 14, and other device forming ingredients, such as is binders, dispersants, wetting agents, lubricants or dyes, with all the ingredients in dosage form 110 equal to 100%.

The terms "low number average molecular weight hydroxy propyl methyl cellulose ether", "high number average molecular weight hydroxy propyl methyl cellulose ether", and "hydroxy propyl cellulose" are used as described in U.S. Pat. No. 4,964,685, column 4, line 7 to column 5, line 9.

Beclomethasone dipropionate can be present in device 110 neat, or in a presently preferred embodiment, with a binder, dispersant, wetting agent, lubricant or dye. The representative materials for these agents that are described with regard to oral osmotic device 10 can be used in oral erosion device 110. Device 110 is manufactured as described in U.S. Pat. No. 4,871,548, column 7, line 14 to line 66.

Figure 7:
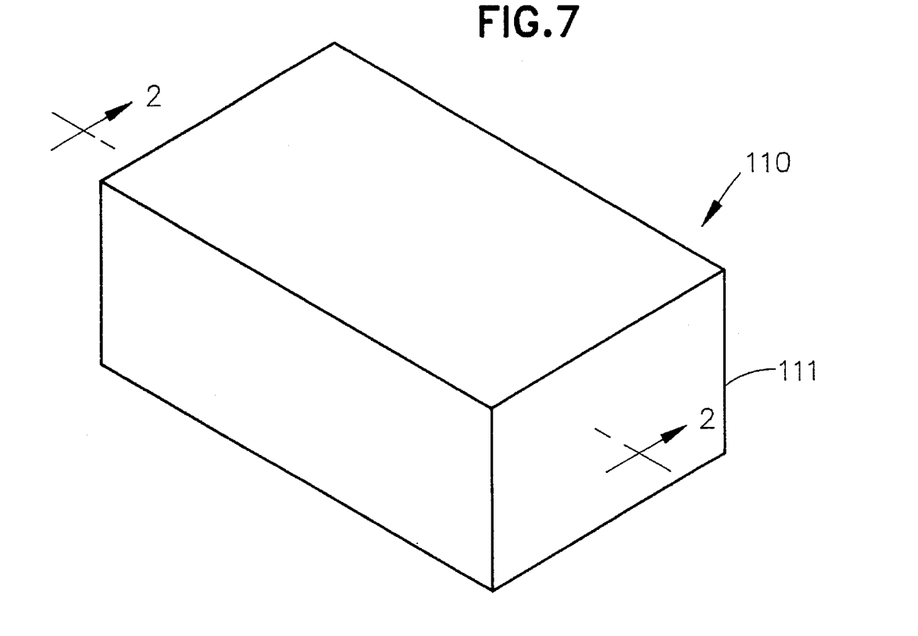
FIG. 7 is a top view of another embodiment of the erosion controlled device for administering beclomethasone dipropionate into is the oral cavity of an animal.

In FIG. 7, erosion device 110 comprises body 111 that is non-toxic and does not adversely affect the buccal tissues of the patient.

Figure 8:
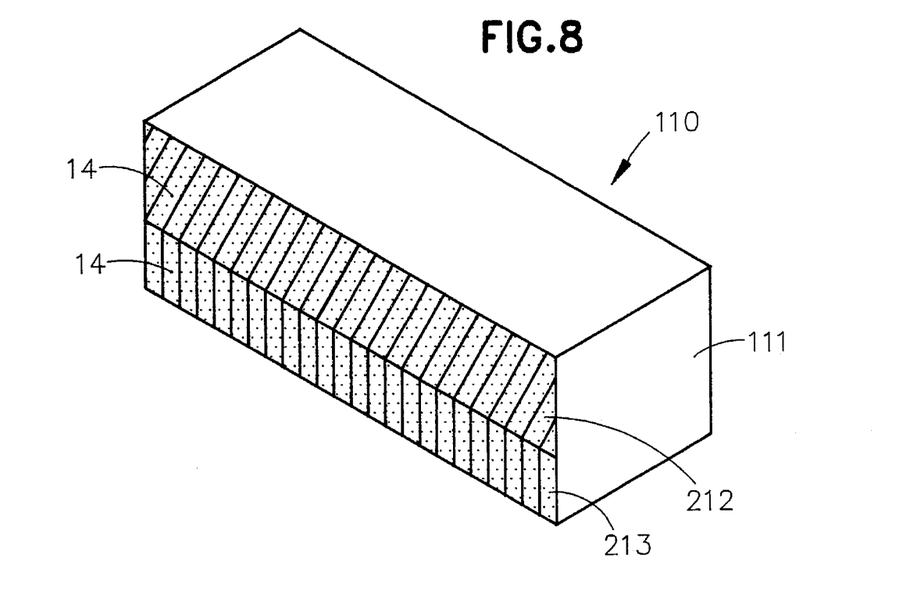
FIG. 8 is a side sectional view of the erosion controlled device of FIG. 7 illustrating the internal structure of the device.

In FIG. 8, erosion device 110 is seen in opened section through 2—2 of FIG. 7. In FIG. 8 device 110 comprises body 111, which body 111 comprises a first lamina 212 and a second lamina 213. First lamina 212 and second lamina 213 are laminated together and function as a single device 110.

Device 110 comprises beclomethasone dipropionate 14 present in at least the first lamina, or present in the second lamina 213 or, optionally, present in both first lamina 212 and second lamina 213. Device 110, comprising lamina 212 and lamina 213, comprises a non-toxic cellulose ether composition, and optionally other pharmaceutically acceptable laminae forming ingredients.

Figure 9:
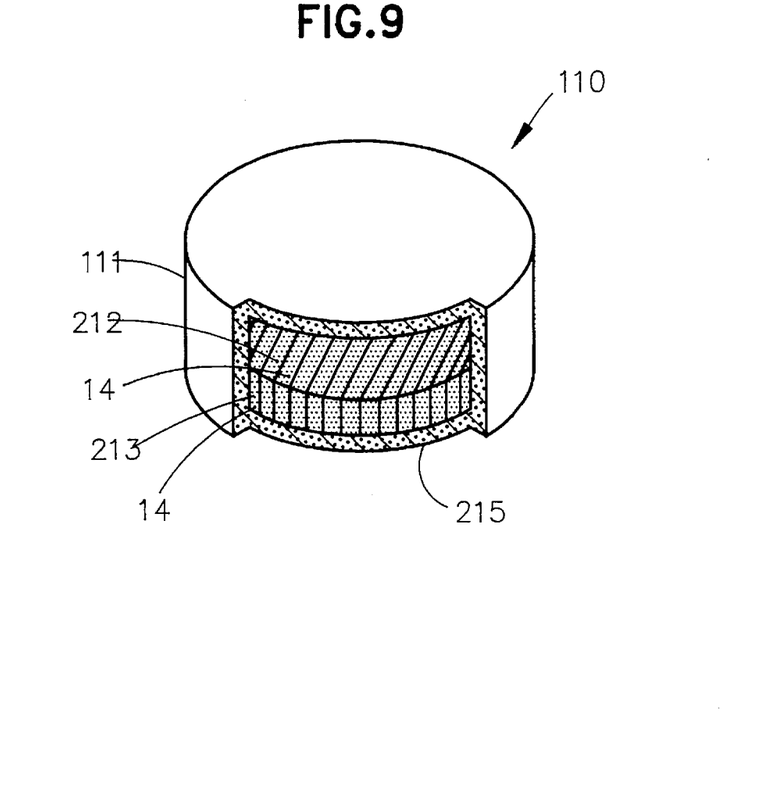
FIG. 9 is a side sectional view of another embodiment of the erosion controlled device for administering beclomethasone dipropionate into the oral cavity of an animal.

FIG. 9 illustrates another embodiment, wherein device 110 comprises body 111, first lamina 212, second lamina 213 and external coat 215. Device 110 comprises beclomethasone dipropionate 14, present in at least the first lamina, or present in the second lamina 213 or, optionally present in both first lamina 212 and second lamina 213. Coat 215 surrounds internal lamina 213 and internal lamina 212. Optionally, beclomethasone dipropionate is present in coat 215.

Device 110 comprises from about 10 wt. % to 90 wt. % of at least one cellulose ether composition based on the total weight of the device. In one embodiment, the cellulose ether composition of device 110 comprises at least one hydroxy propyl methyl cellulose and, optionally, at least one hydroxy propyl cellulose. The hydroxy propyl methyl cellulose comprises a hydroxy propoxyl content of 4% to 12% and a methoxyl content of 19% to 30%. The hydroxy propyl cellulose comprises a hydroxy propoxyl from 7% to 16%. Exemplary hydroxy propyl methyl cellulose and hydroxy propyl cellulose that can be used for forming lamina of this invention are described in U.S. Pat. No. 4,946,685, column 4, line 46 to column 5, line 15.

Lamina 212 of device 110 comprises at least one hydroxy propyl methyl cellulose in an amount of at least 15 wt. % to 80 wt. %, based on the total weight of device 10, or at least 20 wt. % to 80 wt. %, based on the total weight of lamina 212. Lamina 213 of device 110 so comprises at least one hydroxy propyl cellulose, or at least one hydroxy propyl methyl cellulose, in an amount of at least 2 wt. % to 60 wt. %, based on the total weight of device 110, or about 5 wt. % to 50 wt. %, based on the total weight of lamina 213. Lamina 212 and 213 can comprise each a single cellulose ether, a blend of two cellulose ethers, a tertiary blend comprising three cellulose ethers, and the like. Lamina 212 and 213 comprise unlike cellulose ethers. Representative cellulose ether compositions are described in U.S. Pat. No. 4,946,685, column 5, line 33 to column 6, line 54.

Coat 215 comprises at least one hydroxypropyl(alkyl)$_n$-cellulose, wherein n is 0 or 1 and alkyl is straight or branched of 1 to 7 carbon atoms, such as methyl, ethyl, etc., and at least one phamaceutically acceptable plasticizer for imparting flexibility to device 110. Representative plasticizers are described in U.S. Pat. No. 4,946,685, column 7, line 9 to line 15. Generally, from 2% to 40% of plasticizer is mixed with the hydroxypropyl(alkyl)$_n$cellulose. The coating fluid can be spray coated, dip coated, and the like, around the bilaminate.

Beclomethasone dipropionate can be present in device 110 neat, or in a presently preferred embodiment, with other composition and lamina forming ingredients, such as a binder, dispersant, wetting agent, lubricant or dye. Representative materials of these agents described for oral osmotic device 10 can be used in oral erosion device 110, as can the agents described in U.S. Pat. No. 4,946,685, column 7, line 17 to line 29. Device 110 is manufactured as described in U.S. Pat. No. 4,946,685, column 9, line 45 to column 10, line 29.

Figure 10:
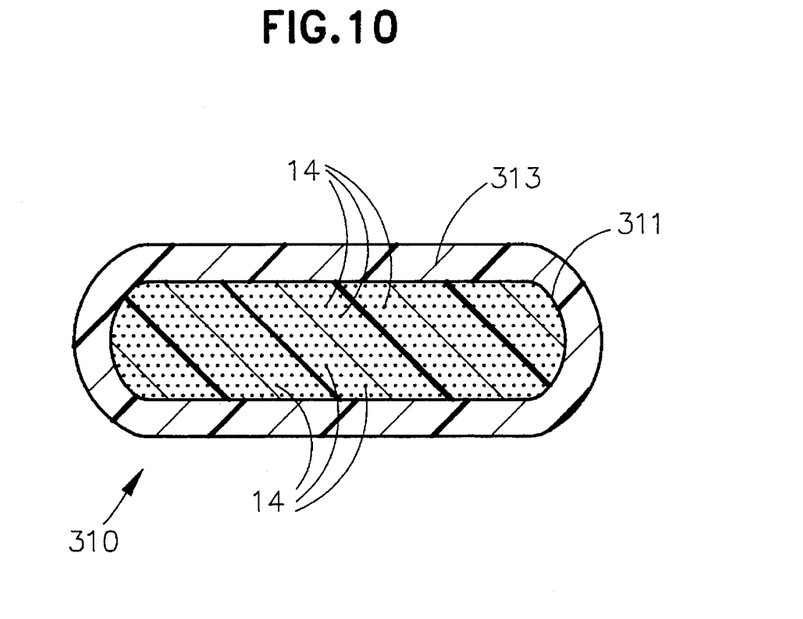
FIG. 10 is a side sectional view of the diffusion controlled device that illustrates the internal structure of the device.

An oral diffusion device suitable for a method of controlled local delivery of beclomethasone dipropionate into the oral cavity for an extended period of time is shown in FIG. 10. In FIG. 10, oral diffusion device 310 comprises a matrix 311, which is non-toxic and does not adversely affect the buccal tissues of the patient, having beclomethasone dipropionate 14 dispersed therethrough. Matrix 311 is surrounded by polymeric membrane 313. In another embodiment of the invention, no polymeric membrane surrounds matrix 311. Both matrix 311 and polymeric membrane 313 are permeable to passage of beclomethasone dipropionate by diffusion, that is, molecules of beclomethasone dipropionate can dissolve in and diffuse through these materials. However, the permeability of matrix 311 to diffusion of beclomethasone dipropionate is greater than that of polymeric membrane 313. Thus, polymeric membrane 313 acts as the rate limiting barrier for beclomethasone dipropionate release.

Materials used to form the membrane are those capable of forming walls through which beclomethasone dipropionate can pass at a relatively low rate. Suitable polymers are biologically compatible and insoluble in body fluid (e.g., salvia). Materials that can be used are described in U.S. Pat. No. 3,854,480, column 3, line 67 to column 4, line 18. Various solid materials can be used to form the solid matrix having particles of beclomethasone dipropionate distributed therethrough. Essentially any solid material chemically compatible with beclomethasone dipropionate and permeable to the passage of it by diffusion can be used. Materials that can be used for the matrix are those polymeric materials set forth above, as suitable for forming the polymeric membrane. Flux enhancers, such as polyvinyl pyrrolidone, hydroxy propyl methyl cellulose, sorbitol and the like, can be added to the matrix to increase its water permeability.

Beclomethasone dipropionate can be present in device 310 neat, or in a presently preferred embodiment, with a binder, dispersant, wetting agent, lubricant or dye. The representative materials that are described with regard to oral osmotic device 10 can be used in oral erosion device 310.

Devices of FIGS. 1–10 are designed for oral use, that is, for locally releasing beclomethasone dipropionate in the oral cavity of an animal, such as a human, over an extended period of time. Because the devices are designed to be retained in the mouth for periods on the order of about 0.5 to 12 hours, the devices must have an exterior shape which is comfortably retained in the mouth. It has been found that an oblong or elliptically shaped device is preferred from a comfort standpoint. As shown in FIGS. 1 and 2, device 10 has a length l, a width w, and a height h. It has been found that devices having an aspect ratio, which ratio is the ratio of l:w, of about 1.2:1 to about 3:1, are most comfortably retained in the mouths of humans. Preferably, the devices have an aspect ratio of about 1.3:1 to about 2:1, and most preferably about 1.5:1 to about 1.7:1. In addition, in order to fit comfortably between the cheek and gum of a patient, the devices have a height of about 0.5 to about 10 mm, preferably about 2 to about 8 mm, and most preferably about 3 to about 5 mm. The devices also have a volume of less than about 2 cm$^3$, preferably about 0.1 to about 0.5 cm$^3$, and most preferably about 0.25 cm$^3$.

The expressions "extended period of time" and "extended delivery period", as used herein, generally refer to periods greater than about 0.5 hours, preferably about 0.5 to 12 hours, more preferably about 1 to 6 hours, most preferably about 2–4 hours.

The phrase "beclomethasone dipropionate formulation" indicates that beclomethasone dipropionate is present in the device accompanied by a gelling or suspending agent, an osmagent, a binder, dye or the like.

Generally, the device has from about 0.05 ng to 500 mg or more of beclomethasone dipropionate, carrier, fillers, excipients, etc. with individual devices containing, for example, 0.25 mg, 1 mg, 5 mg, 125 mg, 250 mg, 500 mg, and the like. Preferably, the device contains about 0.01 mg to about 6 mg beclomethasone dipropionate, most preferably the device contains about 0.1 mg to about 1.0 mg beclomethasone dipropionate. The device releases beclomethasone dipropionate at the rate of about 0.01 mg/hr to about 0.5 mg/hr over the extended delivery period. Preferably, the device releases beclomethasone dipropionate at the rate of about 0.02 mg/hr to about 0.1 mg/hr over the extended delivery period. The device can be administered one to six times a day to a patient, preferably one to two times a day.

All patents and references given the specification are incorporated by reference.

The following examples are merely illustrative of the present invention and should not be considered as limiting the scope of the invention in any way.

EXAMPLE 1

An osmotic therapeutic device for the controlled and continuous release into the oral cavity of the beclomethasone dipropionate was made as follows: 0.22 mg of beclomethasone dipropionate, 167.54 mg of hydroxy propyl cellulose (KLUCEL EF), 71.76 mg of polyvinyl pyrrolidone K29–32, 0.48 mg of magnesium stearate were added to a fluid bed granulator and blended with water to produce a homogenous granulation. The resulting beclomethasone dipropionate formulation had a white color.

Next, the hydrophilic polymer composition of the device was formulated by mixing 124.8 mg of kappa-carrageenan, 22.4 mg sorbitol, 8.0 mg polyvinyl pyrrolidone K29–32, 1.6 mg potassium chloride, 1.6 mg $Fe_2O_3$ as a colorant and 1.6 mg of magnesium stearate in a fluid bed granulator with water.

The beclomethasone dipropionte formulation was fed into the cavity mold of a Manesty® Layer Press and tamped lightly to produce a solid layer. Then, the hydrophilic polymer composition was fed into the cavity overlaying the tamped layer and compressed, using a ⅝ inch oval punch with a pressure head of 2 tons to form a two-layer compartment forming member. The hydrophilic polymer driving layer had a reddish-brown color due to the ferric oxide.

The compartment forming member was coated with a semipermeable wall. The wall was formed by first blending 27 g of cellulose acetate having an acetyl content of 39.8% with 1103 ml of acetone, 100 ml of water and 18 g of polyethylene glycol 3350, and then coating the two layered compartment forming member with this composition in a pan coater, having a 1 kg charge until a 45 mg semipermeable wall surrounded the compartment. The coated device was dried for 72 hours at 35° C., and then one 20 mil passageway was laser drilled through the semipermeable wall to connect the layer of beclomethasone dipropionate with the exterior of the device. The KLUCEL component of the wall material made the wall sufficiently translucent to clearly see the white beclomethasone dipropionate layer and the red hydrophilic polymer layer.

Figure 11:
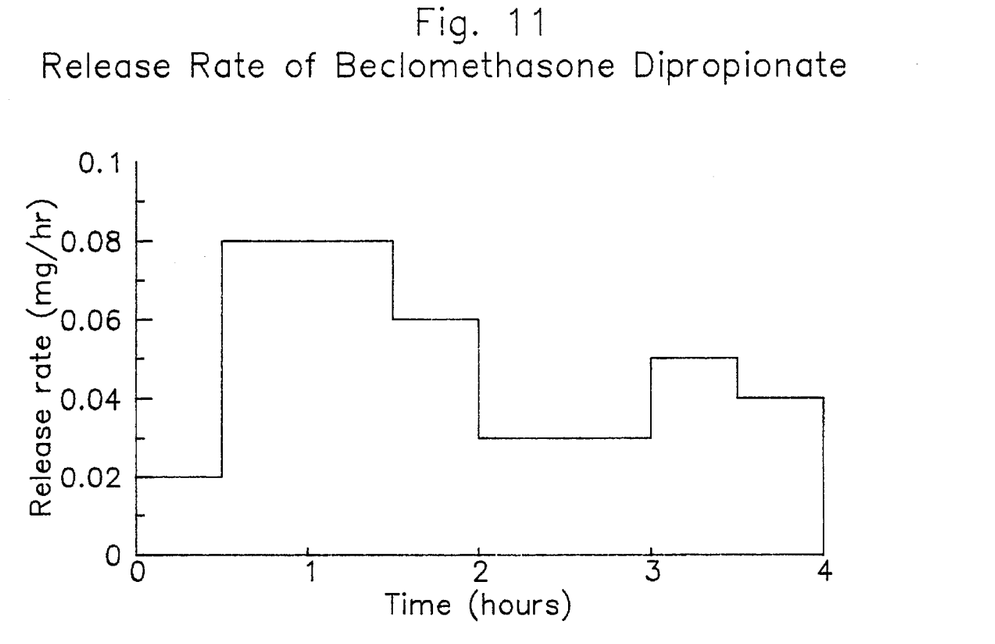
FIG. 11 is a graph depicting the release rate of beclomethasone dipropionate from an osmotic device; and, FIG. 12 is a graph depicting the cumulative amount of beclomethasone dipropionate released over four hours from an osmotic device, In the drawings (which are not drawn to scale) and the specification, like parts in related figures are identified by like so numerals.
Figure 12:
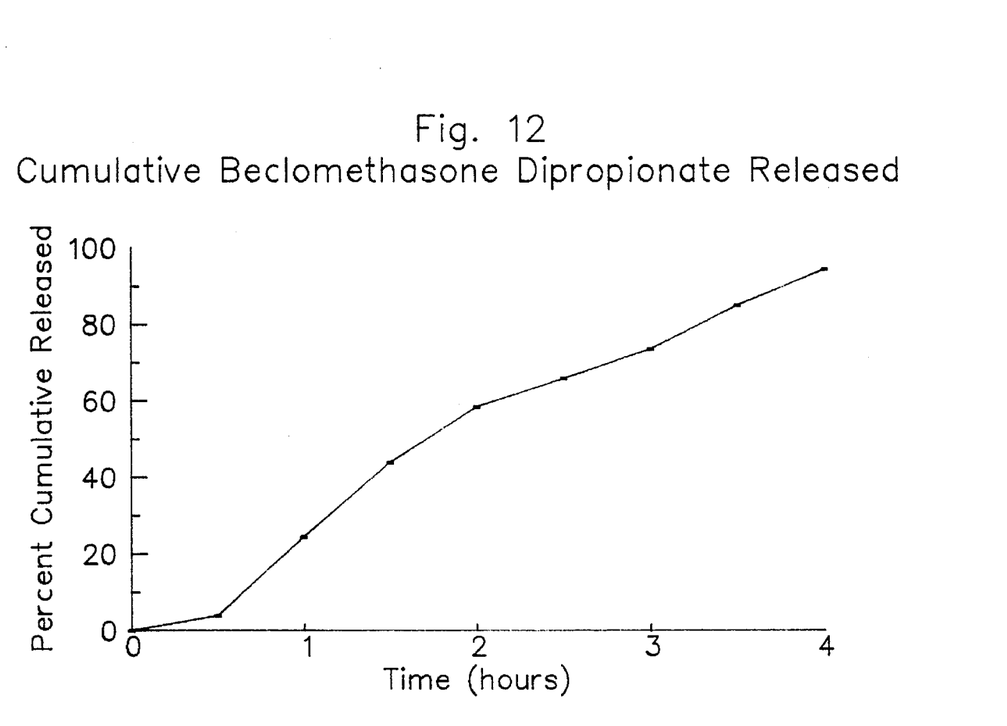

The rate of release of the coated device over a four hour time period, when placed in water at 37° C., is shown in FIG. 11. The cumulative amount of beclomethasone dipropionate released over the four hours is shown in FIG. 12.

To treat oral inflammatory disease by local delivery of beclomethasone dipropionate, the patient holds the oral osmotic device in his mouth for 3 to 4 hours. Two devices are used by the patient per 24 hours. Beclomethasone dipropionate (200 µg) is delivered to the oral cavity at a constant rate for the 3 to 4 hours. When delivery is complete, the entire system turns reddish-brown.

EXAMPLE 2

An osmotic therapeutic device, manufactured in the form of a delivery device for delivering beclomethasone dipropionate into the oral cavity for an extended period of time, was manufactured as follows: first, a 240 mg composition comprising 0.09% beclomethasone dipropionate, 43.80% hydroxy propyl cellulose (KLUCEL EF), 41.06% mannitol, 10.00% polyvinyl pyrrolidone K29–32, 5.00% PGA and 0.50% magnesium stearate was added to a fluid bed granulator and blended with water, to produce a homogenous granulation. The resulting beclomethasone dipropionate formulation had a white color.

Next, a 173 mg hydrophilic polymer composition comprising 55.0% kappa carrageenan, 15.0% polyvinyl pyrrolidone K29–32, 28.0% sorbitol, 0.3% FD&C Blue #1, 0.07% D&C Yellow #10 and 1.0% stearic acid was added to a fluid bed granulator and blended with water to produce a homogenous granulation.

The beclomethasone dipropionate formulation was fed into the cavity mold of a Manesty® Layer Press and tamped lightly to produce a solid layer. Then, the hydrophilic polymer composition was fed into the cavity overlaying the tamped layer and compressed, using a ⅝ inch oval punch with a pressure head of 2 tons to form a two-layer compartment forming member. The hydrophilic polymer driving layer had a green color providing a good color contrast with the white beclomethasone dipropionate containing layer.

Then, the two layered mass was coated in a standard pan coater with a semipermeable polymeric wall formed from a 4% solids solution consisting of 70 wt. % cellulose acetate having an acetyl content of 39.8%, in a solvent consisting of 90% acetone and 10% water, and 30 wt. % polyethylene glycol 3350. The resulting semipermeable wall had a thickness of 5 mils. The KLUCEL component of the wall material made the wall translucent, making it possible to see both the white beclomethasone dipropionate-containing layer and the green hydrogel layer within the inner compartment of the device. Finally, one osmotic passageway, having a diameter of 20 mils, was drilled through the wall facing the beclomethasone dipropionate-containing layer for delivering it from the device.

To treat oral inflammatory disease by local delivery of beclomethasone dipropionate, the patient holds the oral osmotic device in his mouth for 3 to 4 hours. Two devices are used by the patient per 24 hours. Beclomethasone dipropionate (200 µg) is delivered to the oral cavity at a constant rate for the 3 to 4 hours. When delivery is complete the entire system turns green.

EXAMPLE 3

An oral osmotic therapeutic device for delivering beclomethasone dipropionate is manufactured by following the procedure of Example 2, with all conditions and procedures as described, except, in this example, following drilling of the passageway, the device is overcoated with a mixture comprising 0.125 wt. % beclomethasone dipropionate and 99.875 wt. % hydroxy propylmethyl cellulose (HPMCE-5). The overcoating layer has a thickness of 3 mils.

To treat oral inflammatory disease by local delivery of beclomethasone dipropionate, the patient holds the oral osmotic device in his mouth for 3 to 4 hours. Two devices are used by the patient per 24 hours. The beclomethasone dipropionate overcoat provides a loading dose which is quickly delivered to the patient upon retention in the mouth. Generally, the overcoat layer is completely removed by patient sucking within about 15 to 30 minutes. Beclomethasone dipropionate is then delivered to the oral cavity at a constant rate for 3 to 4 hours. When delivery is complete the entire system turns green.

EXAMPLE 4

An erosion controlled device manufactured in the form of an oral delivery device for delivering beclomethasone dipropionate into the oral cavity is manufactured as follows: a 500 mg composition comprising 0.04% beclomethasone dipropionate, 70 wt. % of hydroxy propyl methyl cellulose having a number average molecular weight of 242,000; 20 wt. % of hydroxy propyl methyl cellulose, comprising a number average molecular weight of 19,600 and 9 wt. % of hydroxy propyl cellulose consisting of a hydroxy propoxy content of 13% to 16%, is prepared by blending the ingredients into a homogenous blend. Next, anhydrous methyl alcohol is added slowly with mixing to form a s uniform dough. The dough is passed through a 20 mesh screen and then air dried for 2 hours at room temperature. The resulting granules are repassed through the 20 mesh screen and dried at ambient conditions overnight. Then, magnesium stearate, 1%, is passed through an 80 mesh per inch screen and then is blended in a twin shell mixer for 3 minutes. The resulting granulation is compressed on a D3Band and then pressed into a solid mass in a commercially available Manesty® Press set to a Stoke's hardness of 7 kg.

To treat oral inflammatory disease by local delivery of beclomethasone dipropionate, the patient places the oral erosion device in his mouth. After 2 to 6 hours, the device erodes completely. Two devices are used by the patient per 24 hours. Beclomethasone dipropionate (200 µg) is delivered to the oral cavity at a constant rate over the 2 to 6 hours. Delivery is complete, when the entire system has eroded.

EXAMPLE 5

An erosion controlled device manufactured in the form of an oral delivery device for delivering beclomethasone dipropionate into the oral cavity is manufactured as follows: first, a 500 mg composition having 0.027 wt. % of beclomethasone dipropionate, 70 wt. % of hydroxy propyl methyl cellulose having a number average molecular weight of 242,000; 29 wt. % of hydroxy propyl methyl cellulose having a number average molecular weight of 9,200 and 1.0 wt. % of magnesium stearate is compressed into a first lamina. Then, a second lamina weighing 250 mg having 0.027 wt. % of beclomethasone dipropionate, 98 wt. % hydroxy propyl methyl cellulose with 10–13 wt. % hydroxy propoxy content, 1 wt. % of hydroxy propyl methyl cellulose, having a number average molecular weight of 9,200, and 1.0 wt. % of magnesium stearate is deposited over the first lamina and the second lamina compressed thereto.

To treat oral inflammatory disease by local delivery of beclomethasone dipropionate, the patient places the oral erosion device in his mouth. After 2 to 6 hours, the device erodes completely. Two devices are used by the patient per 24 hours. Beclomethasone dipropionate (200 µg) is delivered to the oral cavity at a constant rate over two to six hours. Delivery is complete, when the entire system has eroded.

While there have been described and pointed out features of the invention as applied to the presently preferred embodiments, those skilled in the art will appreciate that various modifications, changes, additions and omissions in the systems illustrated and described can be made without departing from the spirit and scope of the invention, as defined in the appended claims.

What is claimed is:

1. A method of locally treating oral inflammatory disease comprising:
   retaining an osmotic delivery device in a mouth of an animal over an extended delivery period; and
   controlled delivering of beclomethasone dipropionate to the mouth the animal at a constant rate of about 0.01 mg/hour to about 0.5 mg/hour over the extended delivery period, wherein the delivery period is about 1 to about 6 hours.

2. A method of locally treating oral inflammatory disease comprising:
   retaining an osmotic delivery device within a mouth of an animal for an extended delivery period; and
   controlled delivering of beclomethasone dipropionate to the mouth of the animal at a constant rate of about 0.01 mg/hr to about 0.5 mg/hour over the extended delivery period, wherein the extended delivery period is about 2 to about 4 hours.

3. A method of locally treating oral inflammatory disease comprising:
   retaining an osmotic device in a mouth of an animal for an extended delivery period, the device having a size and shape suitable for comfortably retaining the device in the mouth for the extended delivery period, the device including a wall surrounding and forming a compartment containing (i) a layer of a dose of the beclomethasone dipropionate, wherein the layer of dose further comprises a first and second unlike cellulose ethers, a gelling agent and (ii) a layer of a hydrophilic polymer, and a passageway in the semipermeable wall communicating with the layer of beclomethasone dipropionate in the compartment and with the exterior of the device, the wall being formed of a semipermeable material which is (i) permeable to the passage of the aqueous fluid and (ii) substantially impermeable to the passage of the hydrophilic polymer; and
   controlled delivering of beclomethasone dipropionate, to the mouth of the animal at a constant rate over the extended delivery period.

4. The method of treating oral inflammatory disease according to claim 3, wherein the device includes a mechanism for signaling the animal when the dose of beclomethasone dipropionate has been delivered from the device.

5. The method of treating oral inflammatory disease according to claim 3, wherein the mechanism includes providing the layer of the beneficial agent with a taste which contrasts with the hydrophilic polymer layer taste.

6. The method of treating oral inflammatory disease according to claim 4, wherein the mechanism includes providing the layer of the beclomethasone dipropionate with a color which contrasts with the hydrophilic polymer layer, the semipermeable wall being sufficiently translucent to permit visual inspection of the beclomethasone dipropionate present in the compartment.

7. The method of treating oral inflammatory disease according to claim 3, wherein the wall contains a translucent cellulose polymer.

8. The method of treating oral inflammatory disease according to claim 6, wherein the semipermeable wall has an overcoating containing beclomethasone dipropionate.

9. The method of treating oral inflammatory disease according to claim 1 or 3, wherein the device has a smooth oval shape with an aspect ratio in the range of about 1.2:1 to about 3:1, a height of about 0.5 to about 10 mm, and a volume of less than about 2 cm$^3$.

10. The method of treating oral inflammatory disease according to claim 3, wherein the layer of beneficial agent contains an osmagent.

11. The method of treating oral inflammatory disease according to claim 3, wherein the gelling agent is kappa carrageenan.

12. The method of treating oral inflammatory disease according to claim 3, wherein the hydrophilic polymer is a cross-linked hydrogel.

13. The method of treating oral inflammatory disease according to claim 3, wherein the extended delivery period is about 0.5 to about 12 hours.

14. The method of treating oral inflammatory disease according to claim 3, wherein the extended delivery period is about 1 to about 6 hours.

15. The method of treating oral inflammatory disease according to claim 3, wherein the extended delivery period is about 2 to about 4 hours.

16. A method of locally treating oral inflammatory disease comprising:

retaining an erosion controlled device in a mouth of an animal for an extended delivery period, the device including a body, said body comprising a cellulosic ether formulation, which formulation comprises from 5% to 80% of at least one low number average molecular weight hydroxy propyl methyl cellulose ether and from 10% to 99% of at least one high number average molecular weight hydroxy propyl methyl cellulose ether, and beclomethasone dipropionate; and controlled delivering of beclomethasone dipropionate to the mouth of the animal at a constant rate over the extended delivery period.

17. A method of locally treating oral inflammatory disease comprising:

retaining an erosion controlled device in a mouth of an animal for an extended delivery period, the device including a body, said body comprising a cellulosic ether formulation, which formulation comprises from 5% to 80% of at least one low number average molecular weight hydroxy propyl methyl cellulose ether, from 10% to 99% of at least one high number average molecular weight hydroxy propyl methyl cellulose ether and from 2% to 30% of a hydroxy propyl cellulose, and beclomethasone dipropionate; and controlled delivering of beclomethasone dipropionate to the mouth of the animal at a constant rate over the extended delivery period.

18. A method of locally treating oral inflammatory disease comprising:

retaining in a mouth of an animal for an extended delivery period an erosion controlled device including a bilaminated body, said body comprising a cellulose ether formulation, which formulation comprises a first lamina comprising up to 80 weight percent of a cellulose ether selected from the group of hydroxy propyl methyl cellulose ethers comprising a degree of polymerization of about 50 to about 1260, a viscosity of about 3 to about 100,000 centipoise, and a number average molecular weight of 9,000 to 250,000, and a dosage of beclomethasone of from 0.1 mg to 2 mg; and a second lamina in contacting arrangement with the first lamina, the second lamina comprising up to 50 weight percent of a different cellulose ether composition comprising a hydroxy propyl cellulose comprising a hydroxy propyl content of 7% to 16%; and controlled delivering of beclomethasone dipropionate to the mouth of the animal at a constant rate over the extended delivery period.

19. The method of treating oral inflammatory disease according to claim 18, wherein the device has a coat that surrounds the first lamina and the second lamina, said coat comprising a hydroxypropyl(alkyl)$_n$cellulose, wherein n is 0 to 1 and alkyl comprises 1 to 7 carbon atoms.

20. A method of locally treating oral inflammatory disease comprising:

retaining in a mouth of an animal over an extended delivery period a diffusion controlled device, including a matrix comprising a first and second unlike cellulosic ethers and having solid particles of beclomethasone dipropionate dispersed therethrough, said matrix being permeable to the passage of beclomethasone dipropionate by diffusion and an outer polymeric membrane, insoluble in saliva, surrounding said matrix, said polymeric membrane characterized by being formed of a beclomethasone dipropionate release controlling material which is permeable to the passage of beclomethasone dipropionate, by diffusion, but at a rate which is lower than through said matrix; and controlled delivering of beclomethasone dipropionate to the mouth of the animal at a constant rate over the extended delivery period.

21. The method of treating oral inflammatory disease according to claims 16, 17, 18, 19 or 20, wherein the device has a smooth oval shape with an aspect ratio in the range of about 1.2:1 to about 3:1, a height of about 0.5 to about 10 mm, and a volume of less than about 2 cm$^3$.

22. The method of treating oral inflammatory disease according to claims 16, 17, 18, 19 or 20, wherein the extended delivery period is about 0.5 to about 12 hours.

* * * * *